United States Patent [19]

Rosander

[11] 4,264,303

[45] Apr. 28, 1981

[54] APPARATUS FOR CLEANING AND/OR DISINFECTING SO-CALLED HANDPIECES IN A DENTIST'S EQUIPMENT

[75] Inventor: Jan Rosander, Göteborg, Sweden

[73] Assignee: Scania Dental AB, Knivsta, Sweden

[21] Appl. No.: 35,786

[22] Filed: May 3, 1979

[30] Foreign Application Priority Data

May 19, 1978 [SE] Sweden .............................. 7805748

[51] Int. Cl.³ .............................................. A61C 1/08
[52] U.S. Cl. ...................................... 433/25; 433/114; 433/126
[58] Field of Search ......................... 433/114, 126, 95

[56] References Cited

U.S. PATENT DOCUMENTS

| | | | |
|---|---|---|---|
| 2,039,177 | 4/1936 | McKenzie | 433/114 |
| 2,226,145 | 12/1940 | Smity | 433/95 |

*Primary Examiner*—Robert Peshock
*Attorney, Agent, or Firm*—Hammond & Littell, Weissenberger and Muserlian

[57] ABSTRACT

The invention relates to an apparatus for cleaning and/or disinfecting especially so-called handpieces in a dentist's equipment. The improved apparatus comprises a vessel which is fillable with a suitable liquid or liquid mixture. Said vessel encompasses a rotatably disposed shaft extending through a channel serving as an outlet for the liquid or liquid mixture. There are further means for temporary driving connection with the shaft of the handpiece intended for cleaning and a source for producing a force which, firstly, serves to cause the liquid or liquid mixture, preferably under rotation, to flow out through the channel and then pass through the handpiece, and, secondly, imparts a rotary motion to the shaft, which via a driving connection is transmitted to all of the moving transmission parts of the handpiece.

9 Claims, 4 Drawing Figures

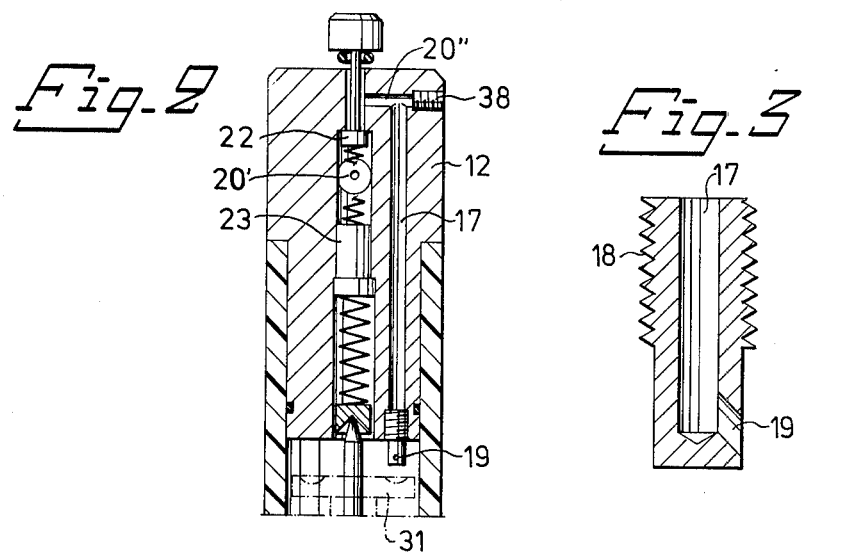
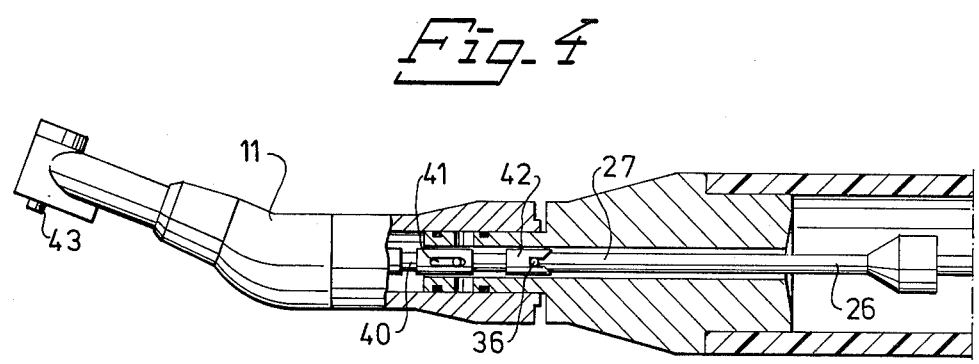

APPARATUS FOR CLEANING AND/OR DISINFECTING SO-CALLED HANDPIECES IN A DENTIST'S EQUIPMENT

Modern dental care makes extensive use of more or less fluid grinding and polishing pastes and diamond or carborundum grinding discs. These grinding agents have a tendency to penetrate, together with blood and saliva, into the handpieces. These implements are precision made, expensive to purchase, and require careful maintenance for reasons of hygiene as well as successful operation. Foreign particles of the above mentioned type wear heavily on transmission parts, such as bearings, shafts and pinions. Blood and saliva also give rise to undesirable bacterial growth. The most common method of cleaning and disinfecting handpieces is to disassemble the implements and clean and disinfect the parts individually. In addition to the fact that such disassembly work is very time consuming, great attention is required when reassembling the implements and even then bearings may be moved out of their original positions and threads can be worn down, and this directly affects the lifetime and reliability of the implements. There has been suggested a method of cleaning handpieces without disassembling them, in which liquid in a pressure container is pressed via a nozzle into the implement to be cleaned. Experience has shown, however, that the cleaning effect is clearly insufficient. Furthermore, the pressurized liquid contains unsuitable propellant gases.

The purpose of the invention is to produce an apparatus for reliable cleaning and/or disinfecting of especially handpieces in a dentist's equipment. Said apparatus is characterized in that it comprises a vessel which can be filled with a suitable liquid or liquid mixture and which is equipped with a rotatably disposed shaft which extends through a channel serving as an outlet for the liquid or liquid mixture, and means for temporary, driving connection with the shaft of the handpiece intended for cleaning, and in that there is a source for producing a force which firstly, serves to cause the liquid or liquid mixture, preferably under rotation, to flow out through the channel and then pass through the handpiece, and secondly, imparts a rotary motion to the shaft which via a driving connection is transmitted to all of the moving transmission parts of the handpiece.

The following advantages are achieved by such a construction:

(a) cleaning and disinfection without disassembly of the implements, (b) all of the transmission parts of the implement are made to rotate during the cleaning process, in combination with the fact that the liquid flows under pressure through the implement to be cleaned, thus achieving practically 100% cleaning/disinfection of the implement, (c) the liquid dissolves blood and saliva, thus satisfying hygienic requirements, (d) great time savings in comparison with methods used up to now, (e) increased lifetime of the implements.

Within the scope of the above definition, a number of practical embodiments are possible. The choice of power source required to press the liquid through the implement which is to be cleaned and/or disinfected, and to set the shaft rotating, is arbitrary. Due to the fact that most dental treatment arrangements normally include a compressor, the following description will describe in detail an embodiment in which the driving force is compressed air.

FIG. 2 is a section along the line II—II in FIG. 1.

FIG. 3 shows in a larger scale the blow channel directed at an angle of about 45° to the vertical plane.

FIG. 4 shows the mechanical connection between an apparatus according to the invention and the implement intended for cleaning.

Figure 1:
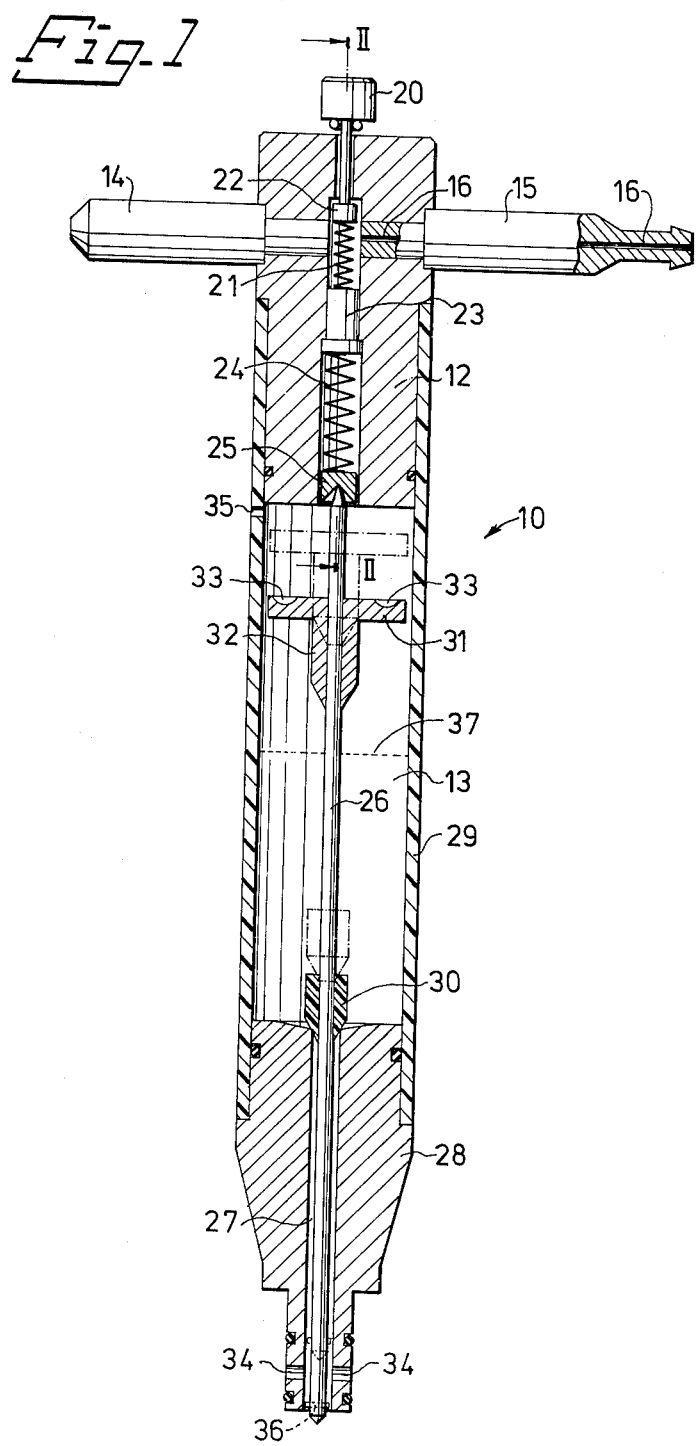
FIG. 1 shows essentially in longitudinal section, an apparatus according to the invention, in which the power source is compressed air.

In the drawing, 10 designates generally an apparatus according to the invention, for cleaning and/or disinfecting of handpieces (generally designated 11 in FIG. 4). These handpieces are called implements in the following and can be pneumatically or electrically driven.

The apparatus according to FIG. 1 comprises a long cylindrical body 12 with an approximately centrally oriented storage space 13 for a liquid or liquid mixture which can be of any desired type, and which does not constitute a part of the present invention. It is only important that the liquid have such characteristics that the intended cleaning and/or disinfection of the interior of the implement 11 takes place.

The upper portion of the apparatus above the storage space 13 can consist of a metallic body and is provided with two handles 14,15, one of which 15 has a hole 16 and has a shape at the end which permits coupling to a hose leading to a source of compressed air (compressor, not shown).

The hole 16 continues into the metallic body and communicates with a vertical hole 17 (FIG. 2), which ends in a nozzle 18 (FIG. 3) from which a blow channel 19, disposed at a certain angle, preferably about 45° relative to the vertical plane, communicates with the storage space 13. An operating valve 20 is influenced by a pressure spring 21.

When the valve 20 is depressed the compressed air is allowed to come into the interior of the apparatus via the blow exit 20', it is pressed upwards and into the channel 20" and then into the hole 17 according to that described above. The pressure spring 21 is pressed between a valve seat 22 and a lower seat 23.

An adjustment screw 38 is arranged to increase or decrease the amount of air from the source of compressed air.

The valve block 12 has a second pressure spring 24 which is pressed between the underside of the seat 23 and the top of a vertically movable bearing 25 with a V-shaped cross section. This bearing will be described in more detail further on.

The bearing 25 bears one end of a longitudinal, displaceably and rotatably disposed shaft 26 which extends through the storage space 13 for the liquid or liquid mixture. The shaft 26 then extends through a channel 27 serving as an outlet for the liquid, which is oriented toward the end, the pointed end of the shaft 26 is situated outside the lower end of the apparatus 10. In the example shown the storage space 13 is an acrylic glass cylinder 29, which, as is shown in the drawing, is joined to the two metallic portions 12 and 28. For discharging excess air there is an opening 35 in the cylinder 29.

The shaft 26 has a lower member 30 fixed to the same with a conical portion and it serves both as a valve for liquid in the storage space 13 by virtue of the fact that the conical portion bears tightly against the upper end of the outlet channel 27, and as a stop for the vertical movement of the shaft in one direction.

The upper portion of the shaft 26 has a disc 31 which is rigidly fixed to the same and is made in one piece with a brace 32. The top side of the disc 31 has a number of cavities 33, whose function and purpose will be described further on. The disc can also be made as a conventional blade wheel.

The lower portion 28 of the apparatus 10 has two opposing openings 34 which function as fill openings for the liquid or liquid mixture which is to be kept in the storage space 13 and which communicate with the channel 27. To fill the storage space of the apparatus 10, a suitable amount of liquid or a mixture of liquids is poured into a vessel (not shown). The apparatus 10 is held vertical so that the free end of the shaft 26 is pressed against the bottom of the vessel. This displaces the shaft 26 upwards and the valve member/stop 30 exposes the end of the channel 27. The liquid flows through the channel 27 into the storage space under its own pressure.

The implement 11 which is to be cleaned and/or disinfexted is of a type which is known per se and is not part of the present invention. The implement 11, which in this example is an angled handpiece, has a rotatable shaft 40 with a connecting member 42 which is displaceable along the slot 41 and is biased by a compression spring (not shown).

For temporary mechanical connection between the apparatus 10 and the implement to be cleaned 11 (see FIG. 4), the displacable and rotatable shaft 26 of the apparatus has at its free end a pin 36 going through the same which cooperates with the connecting member 42.

The apparatus 10 works in the following manner.

When the storage space 13 of the apparatus 10 has been filled with liquid in the manner described above to a certain predetermined level 37, which is always below the disc 31, the apparatus 10 is coupled to the implement 11 in the manner described above and which is shown in FIG. 4. In this connected position, the channel 27 opening is exposed because the shaft 26 is displaced upwards. This second end position is shown with dash-dot lines in FIG. 1 and it can be seen therefrom that the disc 31, which is also rigidly fixed to the shaft 26 has assumed an upper position in which the distance to the nozzle 18 in the valve block 12 is relatively short.

After the operating valve 20 has been depressed, air flows from the source of compressed air in the manner described previously out through the outlet 19 arranged at about at 45° angle relative to the shaft 26. In this manner the air flow strikes the cavities 33 in the top of the disc 31 at said angle with a force whose strength is dependent on the pressure in the source of compressed air. This force imparts a rotary movement to the disc 31 at the same time as part of the force acts on the surface of the liquid 37 via the annular gap between the disc 31 and the interior walls of the cylinder 29. Due to the fact that the disc 31 is rigidly fixed to the shaft 26, the shaft is also imparted a corresponding rotary movement, which is transmitted via the coupling 36, 42 to the rotatable shaft 40 of the implement 11 and the other moving transmission parts therein. The rotary movement of the disc 31 together with the force applied to the surface 37 of the liquid causes the liquid, under powerful rotation in the storage space 13, to be pressed out into the channel 27 and through the annular spaces and gaps in the implement while cleaning and/or disinfecting said spaces/gaps as well as bearings, shafts and pinions in the implement. The liquid then flows out through the opening 43, and carries with it all types of contaminants. By holding the operating valve 20 depressed for a few seconds after all the liquid has been pressed out through the opening 43 in the implement 11, the transmission parts in the implement are blown dry.

The liquid which the apparatus 10 is filled with can be detergent and/or disinfecting and/or contain lubricants for the transmission parts of the implement 11. The liquid as such, however, is not a part of the present invention.

It is obvious that within the scope of the accompanying claims there are other possibilities for implementing the idea of the invention. As a power source one could use an electric motor, which rotates the shaft 26 while a piston mounted on the shaft 26 is displaced vertically at the same time, said piston pressing the liquid through the implement in the manner described above. A precondition is, however, that the shaft 26 must have a threaded connection with such a piston.

Another possibility is to have a source of compressed air rotatably drive a nozzle equipped with a number of outlet openings. In such an embodiment, the disc 31 could be eliminated.

The apparatus according to the invention is especially, but not exclusively intended for cleaning of handpieces in a dentist's equipment.

I claim:

1. An apparatus for cleaning and/or disinfecting dental handpieces having a channel having an inlet end and an outlet end, a shaft rotatable within said channel having a power input and a power output at said inlet end and said outlet end, an output coupling means disengageably coupling said output with a dental tool and an input coupling means for disengageably coupling said power input with a driving power source for rotating said shaft within said channel, said apparatus comprising:
   (a) a vessel adapted to be filled with a cleaning and/or disinfecting liquid,
   (b) a channel means for transferring liquid from said vessel to an outlet cooperating with the inlet end of said handpiece channel,
   (c) pressurizing means acting upon the liquid in said vessel,
   (d) a shaft means rotatable within said vessel and said liquid transferring channel means and extending through said liquid transferring channel means to a free end,
   (e) driving means for rotating said shaft means, and
   (f) connecting means at the free end of said shaft means for releaseably connecting said shaft means with the input coupling means of said handpiece coupling said power input with said rotating shaft means.

2. An apparatus according to claim 1, wherein said shaft means is axially displaceable under the influence of a compression spring and is provided with a valve member bearing, in a non-active position, against an inlet opening of said channel means.

3. An apparatus according to claim 1 wherein a disc-shaped member is arranged on the said shaft means, said member, when said vessel has been filled with liquid, being positioned at a predetermined level above the liquid surface in said vessel.

4. An apparatus according to claim 3 wherein said disc-shaped member is rotatably mounted on said shaft means.

5. An apparatus according to claim 1 wherein said pressurizing means and driving means are operated by a propellant gas, being enclosed in a pressure source and comprising a valve means operable to cause said compressed air to flow via nozzle means into said vessel to apply a pressure on said liquid surface as well as to impart a rotary movement to said shaft means.

6. An apparatus according to claim 3 wherein said disc-shaped member is rigidly joined to said shaft means and is arranged to rotate therewith.

7. An apparatus according to claim 6 wherein the top side of said disc-shaped member is provided with depressions.

8. An apparatus according to claim 5 wherein the air is guided to act on the top side of said disc-shaped member at an angle relative to said shaft means so that the liquid is pressed under rotation out through said channel means.

9. An apparatus according to claim 1 wherein an opening is provided for discharge of excess propellant gas.

* * * * *